US006160013A

United States Patent [19]
Selliah

[11] Patent Number: 6,160,013
[45] Date of Patent: Dec. 12, 2000

[54] 14-AZA PROSTAGLANDINS FOR THE TREATMENT OF GLAUCOMA AND OCULAR HYPERTENSION

[75] Inventor: Robert D. Selliah, Cheshire, Conn.

[73] Assignee: Alcon Laboratories, Inc., Fort Worth, Tex.

[21] Appl. No.: 09/452,044

[22] Filed: Nov. 30, 1999

Related U.S. Application Data

[60] Provisional application No. 60/112,753, Dec. 17, 1998.

[51] Int. Cl.[7] ...................... A61K 31/215; A61K 31/195; C07C 69/74; C07C 405/00
[52] U.S. Cl. .......................... 514/530; 514/532; 514/567; 514/573; 560/42; 560/121; 562/451; 562/503
[58] Field of Search ...................................... 514/530, 532, 514/567, 573; 560/42, 121; 562/451, 503

[56] References Cited

U.S. PATENT DOCUMENTS

| | | | |
|---|---|---|---|
| 4,239,778 | 12/1980 | Venton et al. | 424/305 |
| 4,952,581 | 8/1990 | Bito et al. | 514/236.2 |
| 5,093,329 | 3/1992 | Woodward et al. | 514/469 |
| 5,151,444 | 9/1992 | Ueno et al. | 514/530 |
| 5,387,608 | 2/1995 | Andrews | 514/530 |
| 5,422,368 | 6/1995 | Stjernschantz et al. | 514/530 |
| 5,658,897 | 8/1997 | Burk | 514/118 |
| 5,698,733 | 12/1997 | Hellberg et al. | 560/56 |
| 5,773,471 | 6/1998 | Oguchi et al. | 514/530 |
| 5,807,892 | 9/1998 | Klimko et al. | 514/530 |
| 5,811,443 | 9/1998 | DeSantis et al. | 514/392 |

FOREIGN PATENT DOCUMENTS

| | | |
|---|---|---|
| 0 561073 A1 | 9/1993 | European Pat. Off. . |
| WO 92/08465 | 5/1992 | WIPO . |

OTHER PUBLICATIONS

Alm, The Potential of Prostaglandin Derivatives in Glaucoma Therapy, *Current Opinion in Ophthalmology*, 4(11):44–50 (1993).

Flach et al., Topical Prostaglandin $E_2$ Effects on Normal Human Intraocular Pressure, *Journal of Ocular Pharmacology*, 4(1):13–18 (1988).

Giuffre, The Effects of Prostaglandin $F_{2\alpha}$ the Human Eye, *Graefe's Archive Ophthalmology*, 222:139–141 (1985).

Ichikawa, et al., Molecular Aspects of the Structures and Functions of the Prostaglandin E Receptors, *J. Lipid Mediators Cell Signaling* 14:83–87 (1996).

Kerstetter et al., Prostaglandin $F_{2\alpha}$–1–Isopropylester Lowers Intraocular Pressure Without Decreasing Aqueous Humor Flow, *American Journal of Ophthalmology*, 105:30–34 (1988).

Nakajima et al., Effects of Prostaglandin $D_2$ and its analogue, BW245C, on Intraocular Pressure in Humans, *Graefe's Archive Ophthalmology*, 229:411–413 (1991).

Thierauch et al., Prostaglandins and their Receptors: II. Receptor Structure and Signal Transduction, *Journal of Hypertension*, 12:1–5 (1994).

Waterbury, et al., $EP_3$, But Not $EP_2$, FP, or TP Prostanoid–Receptor Stimulation May Reduce Intraocular Pressure, *Investigative Ophthalmology and Visual Science*, 31(12):2560–2567 (1990).

Woodward et al., Intraocular Pressure Effects of Selective Prostanoid Receptor Agonists Involve Different Receptor Subtypes According to Radioligand Binding Studies, *J. of Lipid Mediators*, 6:545–553 (1993).

Woodward et al., Molecular Characterization and Ocular Hypotensive Properties of the Prostanoid $EP_2$ Receptor, *Journal of Ocular Pharmacology and Therapeutics*, 11(3):447–454 (1995).

*Primary Examiner*—Howard C. Lee
*Assistant Examiner*—Leigh C. Maier
*Attorney, Agent, or Firm*—Barry L. Copeland

[57] ABSTRACT

14-Aza analogs of $PGF_{2\alpha}$, $PGD_2$, and $PGE_2$ and methods of their use in treating glaucoma and ocular hypertension are disclosed.

23 Claims, No Drawings

14-AZA PROSTAGLANDINS FOR THE TREATMENT OF GLAUCOMA AND OCULAR HYPERTENSION

CROSS REFERENCE TO RELATED APPLICATION

This application draws priority from U.S. Provisional Application Ser. No. 60/112,753 filed Dec. 17, 1998.

BACKGROUND OF THE INVENTION

The present invention relates to novel compounds and methods for the treatment of glaucoma and ocular hypertension. In particular, the present invention relates to the use of certain 14-aza analogs of D, E, and F series prostaglandins to treat glaucoma and ocular hypertension.

Glaucoma is a progressive disease which leads to optic nerve damage and, ultimately, total loss of vision. The causes of this disease have been the subject of extensive studies for many years, but are still not fully understood. The principal symptom of and/or risk factor for the disease is elevated intraocular pressure or ocular hypertension due to excess aqueous humor in the anterior chamber of the eye.

The causes of aqueous humor accumulation in the anterior chamber are not fully understood. It is known that elevated intraocular pressure ("IOP") can be at least partially controlled by administering drugs which either reduce the production of aqueous humor within the eye, such as beta-blockers and carbonic anhydrase inhibitors, or increase the outflow of aqueous humor from the eye, such as miotics and sympathomimetics.

Most types of drugs conventionally used to treat glaucoma have potentially serious side effects. Miotics such as pilocarpine can cause blurring of vision and other visual side effects, which may lead either to decreased patient compliance or to termination of therapy. Systemically administered carbonic anhydrase inhibitors can also cause serious side effects such as nausea, dyspepsia, fatigue, and metabolic acidosis, which side effects can affect patient compliance and/or necessitate the termination of treatment. Another type of drug, beta-blockers, have increasingly become associated with serious pulmonary side effects attributable to their effects on beta-2 receptors in pulmonary tissue. Sympathomimetics, on the other hand, may cause tachycardia, arrhythmia and hypertension. Recently, certain prostaglandins and prostaglandin derivatives have been described in the art as being useful in reducing intraocular pressure. Typically, however, prostaglandin therapy for the treatment of elevated intraocular pressure is attended by undesirable side-effects, such as irritation and hyperemia of varying severity and duration. There is therefore a continuing need for therapies which control elevated intraocular pressure associated with glaucoma without the degree of undesirable side-effects attendant to most conventional therapies.

Prostaglandins are metabolite derivatives of arachidonic acid. Arachidonic acid in the body is converted to prostaglandin $G_2$, which is subsequently converted to prostaglandin $H_2$. Other naturally occurring prostaglandins are derivatives of prostaglandin $H_2$. A number of different types of prostaglandins have been discovered including A, B, D, E, F, G, I and J-Series prostaglandins (EP 0 561 073 A1). A number of the naturally occurring prostaglandins, including prostaglandins of the F series (such as $PGF_{2\alpha}$), the E series (such as $PGE_2$) and the D series (such as $PGD_2$) are known to lower IOP after topical ocular instillation, but can cause marked inflammation as evidenced by conjunctival edema or other untoward effects such as conjunctival hyperemia.

All of the natural prostaglandins known to reduce intraocular pressure, including prostaglandins of the F series (such as $PGF_{2\alpha}$), the E series (such as $PGE_2$) and the D series (such as $PGD_2$), have a core cyclopentane ring with alpha and omega chains attached at C-8 and C-12 respectively, as indicated in the following structures:

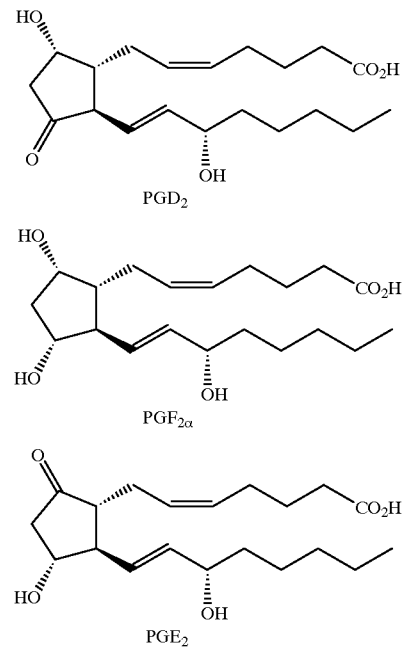

Currently, the relationship between prostaglandin receptor activation and IOP lowering effects is not well understood. Various publications have reported that $PGD_2$ receptor activation leads to second messenger activation and in particular, to the stimulation of adenylate cyclase and resultant increases in cAMP levels (Thierauch, Prostaglandins and their Receptors: II. Receptor Structure and Signal Transduction, *Journal of Hypertension*, volume 12, pages 1–5 (1994). Some believe that $PGF_{2\alpha}$ receptor activation, on the other hand, leads to increased outflow of aqueous humor. Regardless of the mechanism, both $PGD_2$ and $PGF_{2\alpha}$ (and certain of its analogs) have been shown to lower IOP. See (for $PGD_2$) Nakajima, Effects of Prostaglandin $D_2$ and its analogue, BW245C, on Intraocular Pressure in Humans, *Graefe's Archive Ophthalmology*, volume 229, pages 411–413 (1991); and (for $PGF_{2\alpha}$), Giuffre, The Effects of Prostaglandin $F_{2\alpha}$ the Human Eye, *Graefe's Archive Ophthalmology*, volume 222, pages 139–141 (1985); and Kerstetter et al., Prostaglandin $F_{2\alpha}$-1-Isopropylester Lowers Intraocular Pressure Without Decreasing Aqueous Humor Flow, *American Journal of Ophthalmology*, volume 105, pages 30–34 (1988).

Synthetic analogs of both the $PGD_2$ and $PGF_2$ types have been pursued in the art (*Graefe's Archive*

Ophthalmology, volume 229, pages 411–413 (1991)). Although both types of molecules lower IOP, they have also been associated with undesirable side effects resulting from topical ophthalmic dosing. Such effects have included, among others, an initial increase in IOP and conjunctival hyperemia, (Alm, The Potential of Prostaglandin Derivatives in Glaucoma Therapy, *Current Opinion in Ophthalmology*, volume 4, No.11, pages 44–50 (1993)).

The relationship between EP receptor activation and IOP lowering effects is also the subject of some debate. There are currently four recognized subtypes of the EP receptor: $EP_1$, $EP_2$, $EP_3$, and $EP_4$ (*J. Lipid Mediators Cell Signaling*, volume 14, pages 83–87 (1996)). It is known in the art that IOP may be lowered by ligands capable of $EP_2$ receptor activation, such as $PGE_2$ and certain of its synthetic analogs (*Journal of Ocular Pharmacology*, volume 4, number 1, pages 13–18 (1988); *Journal of Ocular Pharmacology and Therapeutics*, volume 11, number 3, pages 447–454 (1995)), or $EP_3$ receptor activation (*Journal of Lipid Mediators*, volume 7, pages 545–553 (1993); *Investigative Ophthalmology and Visual Science*, volume 31, number 12, pages 2560–2567 (1990)). However, some of these molecules have also been associated with undesirable side effects resulting from topical ophthalmic dosing, including an initial increase in IOP, photophobia, and eye ache (see for example *Journal of Ocular Pharmacology*, volume 4, number 1, pages 13–18 (1988)).

A number of synthetic prostaglandins have been observed to lower intraocular pressure, but such compounds also produce the aforementioned side effects in varying degrees which greatly limit their clinical utility. Based on the foregoing, a need exists for the development of molecules that may activate key prostaglandin receptors, yielding a more efficacious lowering of IOP, while exhibiting fewer or reduced side effects.

Attempts have been made by Stjernschantz et al. (U.S. Pat. No. 5,422,368), Woodward et al., (U.S. Pat. No. 5,093,329), Chan et al. (WO 92/08465) and Ueno et al. (U.S. Pat. No. 5,151,444) to reduce selectively or to eliminate altogether the side effects while maintaining the IOP-lowering effect. The Stjernschantz et al. publication is of particular interest because it reports that certain prostaglandin analogs, which possess modifications in the omega chain, still exhibit the intraocular pressure lowering activity of the natural prostaglandins and have fewer adverse effects.

Of interest in the present invention are compounds which are believed to exhibit IOP lowering mechanisms similar to those exhibited by natural D, E, and F series prostaglandins and their synthetic analogs while avoiding some or all of the undesirable side effects usually associated with the use of such compounds. An agent which exhibits comparable or improved efficacy, but with reduced side effects when compared to other agents, is said to have an improved therapeutic profile. It is an object of this invention to provide a novel class of IOP lowering agents with an improved therapeutic profile over the natural prostaglandins and many of their synthetic analogs. A further object of this invention is to provide methods of using the novel compounds in the treatment of glaucoma and ocular hypertension. It has now unexpectedly been discovered that the presently claimed 14-aza analogs of PGD, PGE, and PGF meet this objective.

Certain 14-aza prostanoic acids have been reported (see, U.S. Pat. No. 4,239,778). U.S. Pat. No. 5,387,608 discloses certain 14-sulfonamido prostaglandin analogs for the treatment of glaucoma, and U.S. Pat. No. 5,422,368, mentioned above, discloses prostaglandin analogs in which the omega chain, beyond C-14, may be interrupted with 1–2 heteratoms of oxygen, sulfur and/or nitrogen. The novel compounds of the present invention, however, are neither disclosed nor suggested in the foregoing art.

SUMMARY OF THE INVENTION

The present invention is directed to novel compounds and compositions, and methods of their use in treating glaucoma and ocular hypertension. In particular, the present invention provides certain classes of 14-aza analogs of prostaglandins, and methods of their use in treating glaucoma and ocular hypertension.

DETAILED DESCRIPTION OF THE INVENTION

It has unexpectedly been found that 14-aza prostaglandin analogs of the present invention exhibit an improved therapeutic profile in the treatment of glaucoma and ocular hypertension when compared to natural (C-14) prostaglandins and many of their known analogs. The 14-aza prostaglandin analogs of the present invention may also be used to treat optic nerve disorder by retarding visual field loss or improving visual acuity in the manner described in U.S. Pat. No. 5,773,471, the disclosure of which is incorporated herein by this reference.

It is further contemplated that the compounds of the present inventions can be used with other medicaments known to be useful in the treatment of glaucoma or ocular hypertension, either separately or in combination. For example, the 14-aza prostaglandin analogs of the present invention can be combined with (i) beta-blockers, such as timolol, betaxolol, levobunolol and the like (see U.S. Pat. No. 4,952,581); (ii) carbonic anhydrase inhibitors, such as brinzolamide; (iii) adrenergic agonists including clonidine derivatives, such as apraclonidine or brimonidine (see U.S. Pat. No. 5,811,443); and (iv) cholinergic agonists, such as pilocarpine. The disclosures of U.S. Pat. Nos. 4,952,581 and 5,811,443 are incorporated herein by this reference.

The 14-aza analogs of the present invention have the following formula I:

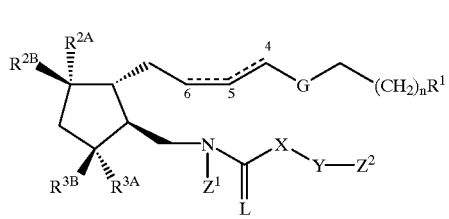

wherein:
  $R^1 = CO_2R$, $CONR^4R^5$, $CH_2OR^6$, or $CH_2NR^7R^8$; where:
    R=H or cationic salt moiety, or $CO_2R$ forms a pharmaceutically acceptable ester moiety;
  $R^4$, $R^5$=same or different=H or alkyl;
  $R^6$=H, acyl, or alkyl;

$R^7$, $R^8$=same or different=H, acyl, or alkyl; with the proviso that if one of $R^7$, $R^8$=acyl, then the other=H or alkyl;

n=0 or 2;

G=$CH_2$ or O;

$R^{2A}$=H, OH, acyloxy, alkoxy;

$R^{2B}$=H, halogen, OH, acyloxy, alkoxy, with the provisos that if $R^{2B}$=halogen, then $R^{2A}$=H, and that $R^{2A}$ and $R^{2B}$ cannot both be from the group consisting of: OH, acyloxy, and alkoxy;

or, $R^{2A}R^{2B}$ taken together=O;

$R^{3A}$=H, OH, acyloxy, alkoxy;

$R^{3B}$=H, halogen, OH, acyloxy, alkoxy, with the provisos that if $R^{3B}$=halogen, then $R^{3A}$=H, and that $R^{3A}$ and $R^{3B}$ cannot both be from the group consisting of: OH, acyloxy, and alkoxy;

or, $R^{3A}R^{3B}$ together=O;

with the further provisos: that if one of $R^{2B}$, $R^{3B}$=halogen, then the other=H; that if one of $R^{2A}R^{2B}$ taken together or $R^{3A}R^{3B}$ taken together=O, then the other≠O; and that $R^{2A}$, $R^{2B}$, $R^{3A}$, $R^{3B}$ cannot all=H;

- - - =single or non-cumulated double bond, with the proviso that when G=O, a single bond exists between carbons 4 and 5;

$Z^1$=H or $CH_3$;

L=O or S;

X=O, S, NH, $CH_2$, or a direct bond;

Y=O, S, NH, $CH_2$, or a direct bond;

with the provisos that Y=$CH_2$ or a direct bond when X=O, S, or NH, and that X $CH_2$ or a direct bond when Y=O, S, or NH;

$Z^2$=$(CH_2)_n CH_3$, cycloalkyl, heteroaryl, or phenyl, the heteroaryl or phenyl being optionally substituted with alkyl, halo, trihalomethyl, alkoxy, acyl, acyloxy, amino, alkylamino, acylamino, or hydroxy;

n=0–5;

or, $Z^2$=$(CH_2)_p Y^1$; where p=0–6; and

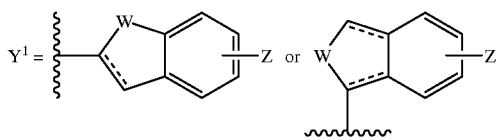

wherein:

W=$CH_2$, O, $S(O)_m$, $NR^9$, $CH_2CH_2$, CH=CH, $CH_2O$, $CH_2S(O)_m$, CH=N, or $CH_2NR^9$; where m=0–2, and $R^9$=H, alkyl, or acyl;

Z=H, alkyl, alkoxy, acyl, acyloxy, halo, trihalomethyl, amino, alkylamino, acylamino, or hydroxy; and

- - - =single or double bond.

Included within the scope of the present invention are the individual enantiomers of the title compounds, as well as their racemic and non-racemic mixtures. The individual enantiomers can be produced by any one of a number of methods, e.g., by purification of a racemic sample by chiral HPLC (A Practical Guide to Chiral Separations by HPLC, G. Subramanian, Ed., VCH Publishers: New York, 1994; Chiral Separations by HPLC, A.M. Krstulovic, Ed., Ellis Horwood Ltd. Publishers, 1989), or by enantioselective hydrolysis of a racemic carboxylic acid ester by an enzyme (Ohno, M.; Otsuka, M. *Organic Reactions*, volume 37, page 1 (1989)). Also included within the scope of the present invention are the individual isomers substantially free of their respective enantiomers.

As used herein, the term "pharmaceutically acceptable ester" means any ester that would be suitable for therapeutic administration to a patient by any conventional means without significant deleterious health consequences; and "ophthalmically acceptable ester" means any pharmaceutically acceptable ester that would be suitable for ophthalmic application, i.e. non-toxic and non-irritating. Wavy line attachments indicate that the configuration may be either alpha (α) or beta (β). The carbon numbering is as indicated in formula I, even when n=2. Dashed lines on bonds [e.g., between carbons 4 (C-4) and 5 (C-5] indicate a single or double bond. Two solid lines present specify the configuration of the relevant double bond. Hatched lines indicate the α configuration. A solid triangular line indicates the β configuration.

The term "acyl" represents a group that is linked by a carbon atom that has a double bond to an oxygen atom and single bond to another carbon atom.

The term "acylamino" represents a group that is linked by an amino atom that is connected to a carbon atom has a double bond to an oxygen group and a single bond to a carbon atom or hydrogen atom The term "acyloxy" represents a group that is linked by an oxygen atom that is connected to a carbon that has a double bond to an oxygen atom and single bond to another carbon atom.

The term "alkenyl" includes straight or branched chain hydrocarbon groups having 1 to 15 carbon atoms with at least one carbon-carbon double bond. The chain hydrogens may be substituted with other groups, such as halogen. Preferred straight or branched alkeny groups include, allyl, 1-butenyl, 1-methyl-2-propenyl and 4-pentenyl.

The term "alkoxy" represents an alkyl group attached through an oxygen linkage.

The term "alkyl" includes straight or branched chain aliphatic hydrocarbon groups that are saturated and have 1 to 15 carbon atoms. The alkyl groups may be substituted with other groups, such as halogen, hydroxyl or alkoxy. Preferred straight or branched alkyl groups include methyl, ethyl, propyl, isopropyl, butyl and t-butyl.

The term "alkylamino" represents an alkyl group attached through a nitrogen linkage.

The term "alkynyl" includes straight or branched chain hydrocarbon groups having 1 to 15 carbon atoms with at least one carbon-carbon triple bond. The chain hydrogens may be substituted with other groups, such as halogen. Preferred straight or branched alkynyl groups include, 2-propynyl, 2-butynyl, 3-butynyl, 1-methyl-2-propynyl and 2-pentynyl.

The term "aryl" refers to carbon-based rings which are aromatic. The rings may be isolated, such as phenyl, or fused, such as naphthyl. The ring hydrogens may be substituted with other groups, such as lower alkyl, or halogen.

The term "carbonyl" represents a group that has a carbon atom that has a double bond to an oxygen atom.

The term "carbonylalkoxy" represents a group that is linked by a carbon atom that has a double bond to an oxygen atom and a single bond to an alkoxy group.

The term "carbonyloxyl" represents a group that is linked by a carbon atom that has a double bond to an oxygen atom and a single bond to a second oxygen atom.

The term "cycloalkyl" includes straight or branched chain, saturated or unsaturated aliphatic hydrocarbon groups which connect to form one or more rings, which can be fused or isolated. The rings may be substituted with other groups, such as halogen, hydroxyl or lower alkyl. Preferred cycloalkyl groups include cyclopropyl, cyclobutyl, cylopentyl and cyclohexyl.

The term "dialkylamino" represents two alkyl groups attached through a nitrogen linkage.

The term "halogen" and "halo" represents fluoro, chloro, bromo, or iodo.

The term "heteroaryl" refers to aromatic hydrocarbon rings which contain at least one heteroatom such as O, S, or N in the ring. Heteroaryl rings may be isolated, with 5 to 6 ring atoms, or fused, with 8 to 10 atoms. The heteroaryl ring(s) hydrogens or heteroatoms with open valency may be substituted with other groups, such as lower alkyl or halogen. Examples of heteroaryl groups include imidazole, pyridine, indole, quinoline, furan, thiophene, pyrrole, tetrahydroquinoline, dihydrobenzofuran, and dihydrobenzindole.

The term "lower alkyl" represents alkyl groups containing one to six carbons ($C_1$–$C_6$).

Preferred compounds of the present invention are those of formula I above, wherein:

$R^1$=$CO_2R$, where R=H or $CO_2R$ forms an ophthalmically acceptable ester moiety;

n=0;

G=$CH_2$ or O, with the proviso that G=$CH_2$ when $R^{2A}$=OH;

---=a single or non-cumulated double bond, with the provisos that a double bond between carbons 4 and 5 may not be of the trans configuration and that a single bond exists between carbons 4 and 5 when G=O;

$R^{2A}$=OH, and $R^{2B}$=H; or $R^{2A}$=H, and $R^{2B}$=Cl;

$R^{3A}$=OH, and $R^{3B}$=H;

$Z^1$=H;

L=O;

X=$CH_2$ or a direct bond;

Y=$CH_2$, O, or a direct bond; and $Z^2$=phenyl optionally substituted with halo or trihalomethyl;

or $Z^2$=cyclohexyl;

or $Z^2$=$Y^1$, where

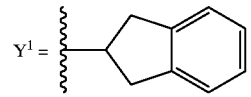

Most preferred of the foregoing compounds are those having an ophthalmically acceptable ester moiety of the formula $CO_2R$, wherein R is alkyl, preferably $C_2$–$C_4$ alkyl, and especially isopropyl. Examples of such most preferred compounds are the following:

| Compound Number | Compound Name | Compound Structure |
|---|---|---|
| II | (5Z)-(9S,11R)-14-Aza-9,11 dihydroxy-15-oxo-17-phenyl-18,19,20-trinor-5-prostenoic acid isopropyl ester | 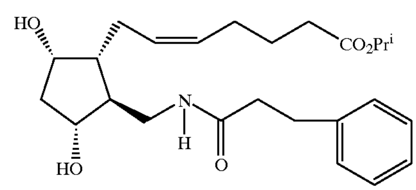 |
| III | (5Z)-(9S,11R)-14-Aza-16-(3-chlorophenoxy)-9,11-dihydroxy-15-oxo-17,18,19,20-tetranor-5-prostenoic acid isopropyl ester | 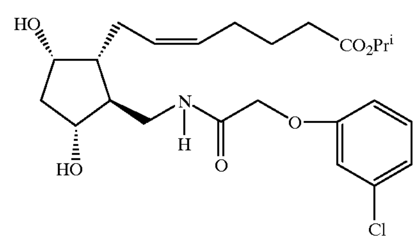 |
| IV | (4Z)-(9S,11R)-14-Aza-16-(3-chlorophenoxy)-9,11-dihydroxy-15-oxo-17,18,19,20-tetranor-4-prostenoic acid isopropyl ester | 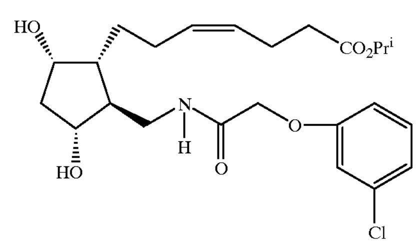 |

-continued

| Compound Number | Compound Name | Compound Structure |
|---|---|---|
| V | (5Z)-(9R,11R)-14-Aza-9-chloro-15-cyclohexyl-9,11-dihydroxy-3-oxa-15-oxo-5-prostenoic acid isopropyl ester | 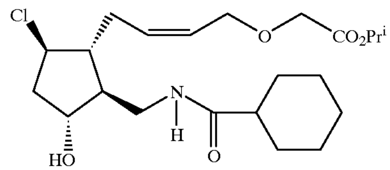 |

In the following Examples 1–4, the following standard abbreviations are used:

g=grams (mg=milligrams); mol=moles (mmol=millimoles); mL=milliliters;

mm Hg=millimeters of mercury; mp=melting point; bp=boiling point; h=hours;

and min=minutes. In addition, "NMR" refers to nuclear magnetic resonance spectroscopy and "MS" refers to mass spectrometry.

EXAMPLE 1

Synthesis of II

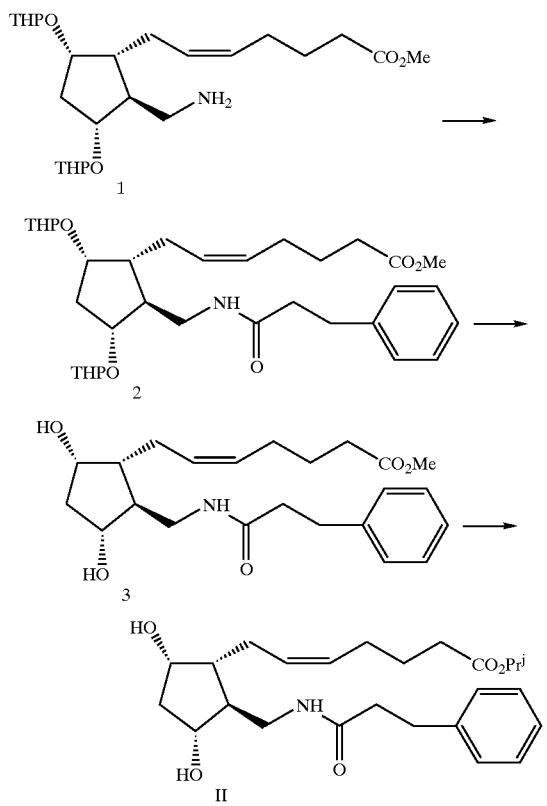

(5Z)-(9S,11R)-14-Aza-9, 11-dihydroxy-15-oxo-17-phenyl-18,19,20-trinor-5-prostenoic acid isopropyl ester (II)

Amine 1 (for the synthesis of 1, see U.S. Pat. No. 5,387,608) is acylated with 3-phenylpropionic acid in the presence of dicyclohexylcarbodiimide (DCC) and 4-(dimethylamino)pyridine (DMAP) in THF to afford amide 2, which is deprotected using catalytic p-toluenesulfonic acid monohydrate (TsOH) in hot THF/water to afford diol 3. Treatment of 3 with Ti(OPr$^i$)$_4$ in refluxing isopropanol provides II.

EXAMPLE 2

Synthesis of III

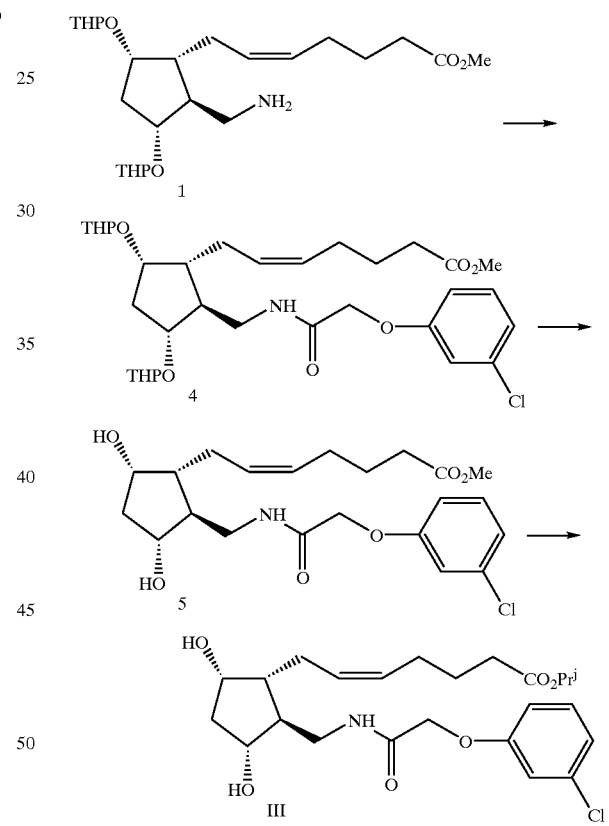

(5Z)-(9S,11R)-14-Aza-16-(3-chlorophenoxy)-9,11-dihydroxy-15-oxo-17,18,19,20-tetranor-5-prostenoic acid isopropyl ester (III)

Acylation of acid 2 with 2-(3-chlorophenoxy)acetic acid [prepared by treatment of ethyl bromoacetate with 3-chlorophenol in refluxing K$_2$CO$_3$/acetone overnight, followed by saponification of the resulting ethyl 2-(3-chlorophenoxy)acetate with LiOH in methanol/water] in the presence of DCC and DMAP in THF provides amide 4, which is deprotected using TsOH in hot THF/water to afford diol 5. Treatment of 5 with Ti(OPr$^i$)$_4$ in refluxing isopropanol provides III.

EXAMPLE 3

Synthesis of IV

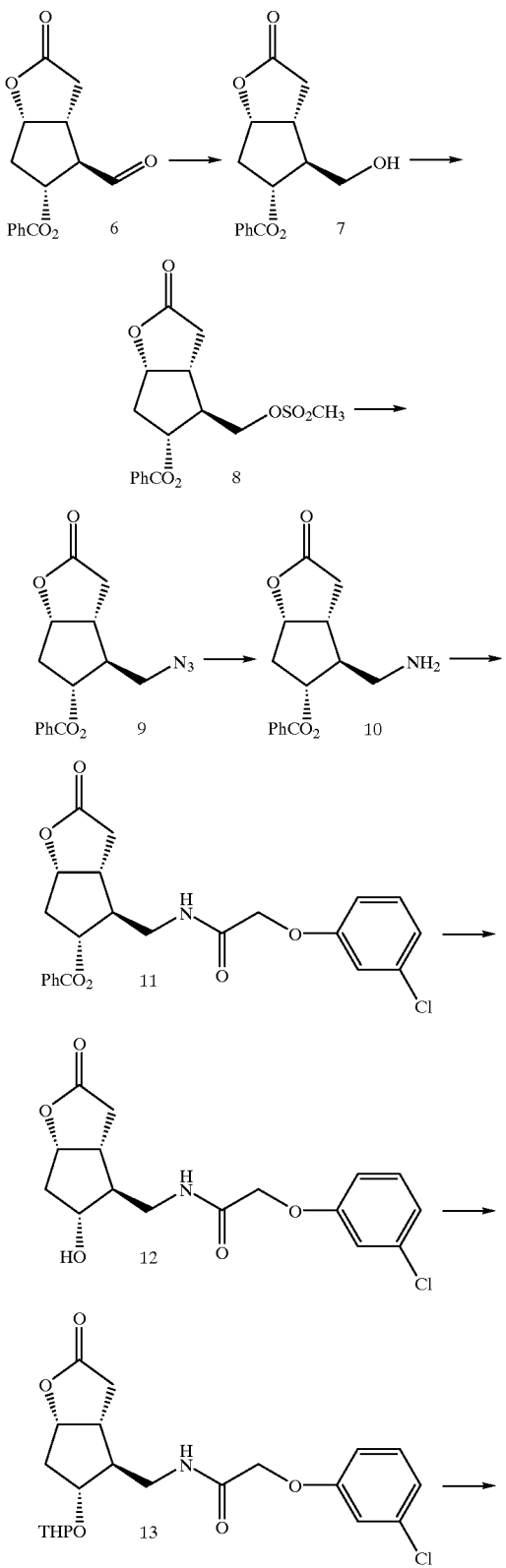

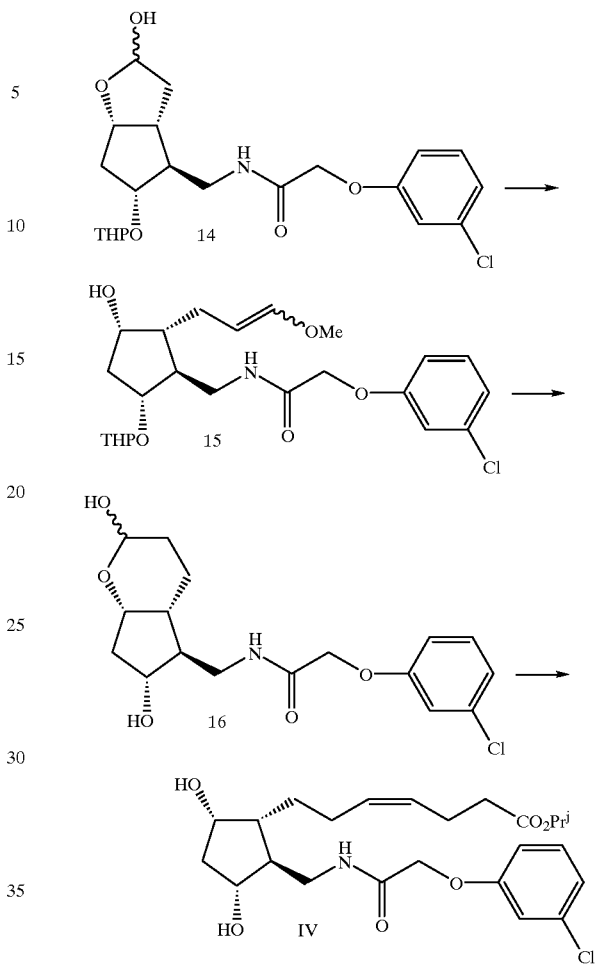

(4Z)-(9 S,11R)-14-Aza-16-(3-chlorophenoxy)-9,11-dihydroxy-15-oxo-17,18,19,20-tetranor-4-prostenoic acid isopropyl ester (IV)

Reduction of aldehyde 6 with $NaBH_4$ in MeOH affords alcohol 7, which is reacted with $CH_3SO_2Cl$ in $CH_2Cl_2$ in the presence of $NEt_3$ to provide mesylate 8. 8 is treated with $NaN_3$ in DMF to give azide 9, which is reduced with $PPh_3$ to yield amine 10. Acylation of amine 10 with 2-(3-chlorophenoxy)acetic acid in the presence of DCC and DMAP affords amide 11, which is debenzoylated using $K_2CO_3$ in MeOH to provide alcohol 12. Treatment of 12 with 3,4-dihydro-2H-pyran in $CH_2Cl_2$ in the presence of catalytic TsOH gives THP ether 13, which is reduced to lactol 14 using diisobutylaluminum hydride in toluene at −78° C. Wittig condensation of 14 with $Ph_3P^+CH_2OMe\ Cl^-$ in THF in the presence of potassium t-butoxide yields enol ether 15, which is converted to diol 16 by reaction with TsOH in hot THF/water. Wittig condensation of 16 with $Ph_3P^+(CH_2)_4CO_2H\ Br^-$ in THF in the presence of potassium t-butoxide, followed by alkylation of the resulting enecarboxylic acid with isopropyl iodide in acetone in the presence of 1,8-diazabicyclo[5.4.0]undec-7-ene affords IV.

EXAMPLE 4

Synthesis of V

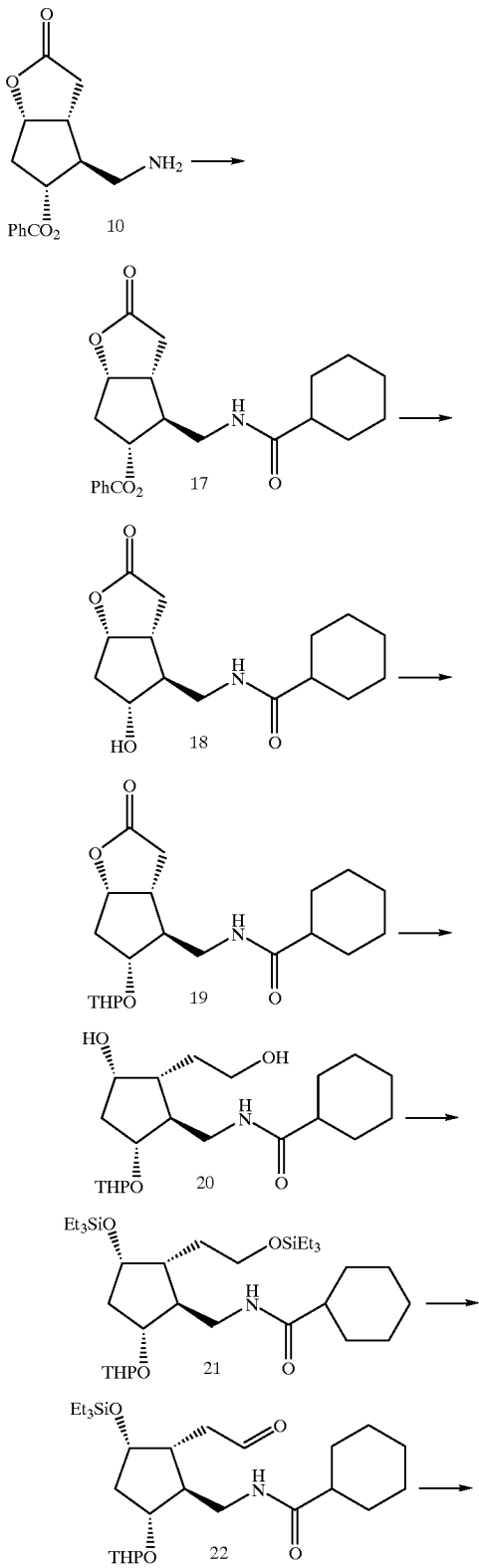
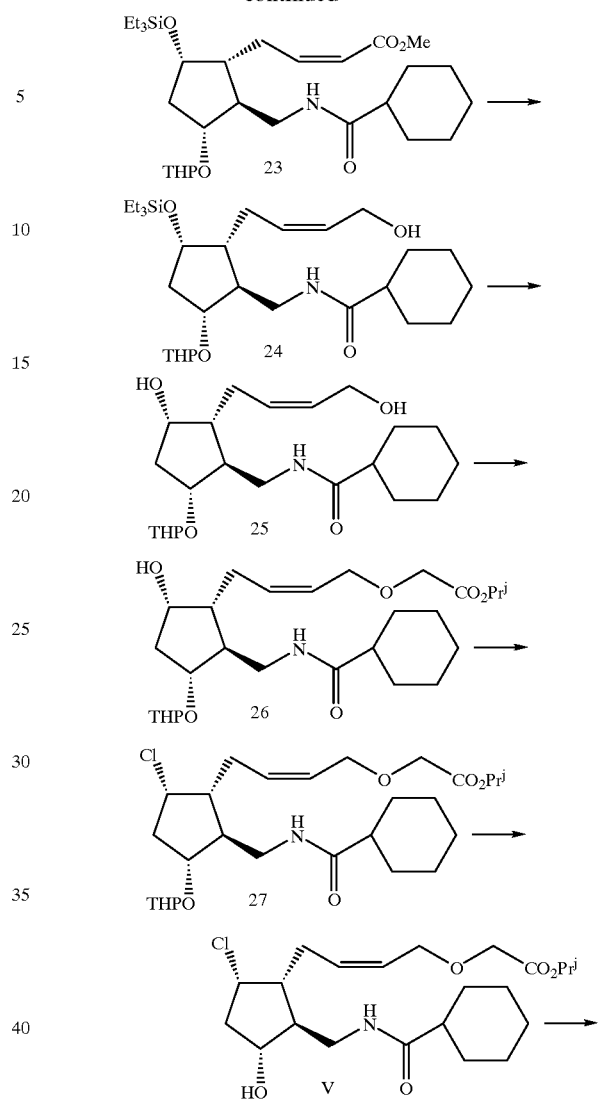

(5Z)-(9R,11R)-14-Aza-9-chloro-15-cyclohexyl-9,11-dihydroxy-3-oxa-15-oxo-5-prostenoic acid isopropyl ester (V)

Amine 10 is acylated with cyclohexanecarboxylic acid in the presence of DCC and DMAP to give amide 17, which is debenzoylated using methanolic $K_2CO_3$ to provide alcohol 18. Treatment of 18 with 3,4-dihydro-2H-pyran in $CH_2Cl_2$ in the presence of TsOH affords ether 19, which is reduced to diol 20 using $LiAlH_4$ in THF. Reaction of 20 with two equivalents of $Et_3SiCl$ in the presence of imidazole and DMAP gives bissilyl ether 21, which is oxidized to aldehyde 22 using $(COCl)_2$/DMSO/$NEt_3$ in $CH_2Cl_2$ at −78° C. Condensation of 22 with $(CF_3CH_2O)_2P(O)CH_2CO_2Me$ in THF at −78° C. in the presence of $KN(SiMe_3)_2$ and 18-crown-6 provides enoate 23, which is reduced to allyl alcohol 24 using diisobutylaluminum hydride in THF at 0° C. Desilylation of 24 using tetra-n-butylammonium fluoride in THF affords diol 25, which is alkylated with $BrCH_2CO_2Pr^i$ in toluene/water in the presence of KOH and $Bu_4NCl$ to give ester 26. Treatment of 26 with $PPh_3$ and $CCl_4$ in $CH_3CN$ provides chloride 27, which is deprotected using TsOH in hot THF/water to give V.

The prostaglandins of the present invention may be formulated in various pharmaceutical compositions for administering to humans and other mammals as a treatment of glaucoma or ocular hypertension. As used herein, the term "pharmaceutically effective amount" refers to that amount of a compound of the present invention which lowers IOP when administered to a patient, especially a mammal. The preferred route of administration is topical. The compounds of the present invention can be administered as solutions, suspensions, or emulsions (dispersions) in an ophthalmically acceptable vehicle. As used herein, the term "ophthalmically acceptable vehicle" refers to any substance or combination of substances which are non-reactive with the compounds and suitable for administration to a patient. Solubilizers and stabilizers are deemed to be non-reactive. Preferred are aqueous vehicles suitable for topical application to the patient's eyes.

In forming compositions for topical administration, the compounds of the present invention are generally formulated as between about 0.00003 to about 0.5 percent by weight (wt %) solutions in water at a pH between 4.5 to 8.0, preferably between about 7.0 and 7.5. The compounds are preferably formulated as between about 0.0005 to about 0.03 wt % and, most preferably, between about 0.001 and about 0.01 wt %. While the precise regimen is left to the discretion of the clinician, it is recommended that the resulting solution be topically applied by placing one drop in each eye one or two times a day.

Other ingredients which may be desirable to use in the ophthalmic preparations of the present invention include preservatives, co-solvents, and viscosity building agents.

Antimicrobial Preservatives:

Ophthalmic products are typically packaged in multidose form. Preservatives are thus required to prevent microbial contamination during use. Suitable preservatives include: benzalkonium chloride, thimerosal, chlorobutanol, methyl paraben, propyl paraben, phenylethyl alcohol, edetate disodium, sorbic acid, Onamer M, or other agents known to those skilled in the art. Such preservatives are typically employed at a level between about 0.001% and about 1.0% by weight.

Co-Solvents:

Prostaglandins, and particularly ester derivatives, typically have limited solubility in water and therefore may require a surfactant or other appropriate co-solvent in the composition. Such co-solvents include: Polysorbate 20, 60 and 80; Pluronic F-68, F-84 and P-103; CREMOPHORE® EL (polyoxyl 35 castor oil) cyclodextrin; or other agents known to those skilled in the art. Such co-solvents are typically employed at a level between about 0.01% and about 2% by weight.

Viscosity Agents:

Viscosity greater than that of simple aqueous solutions may be desirable to increase ocular absorption of the active compound, to decrease variability in dispensing the formulations, to decrease physical separation of components of a suspension or emulsion of formulation and/or otherwise to improve the ophthalmic formulation. Such viscosity building agents include, for example, polyvinyl alcohol, polyvinyl pyrrolidone, methyl cellulose, hydroxy propyl methyl cellulose, hydroxyethyl cellulose, carboxymethyl cellulose, hydroxy propyl cellulose, chondroitin sulfate and salts thereof, hyaluronic acid and salts thereof, and other agents known to those skilled in the art. Such agents are typically employed at a level between about 0.01% and about 2% by weight.

Preferred formulations of the prostaglandins of the present invention include the following Examples 5–7:

EXAMPLE 5

| Ingredient | Amount (wt %) |
| --- | --- |
| Compound III | 0.01 |
| Phosphate Buffered Saline | 1.0 |
| Polysorbate 80 | 0.5 |
| Purified water | q.s. to 100% |

EXAMPLE 6

| Ingredient | Amount (wt %) |
| --- | --- |
| Compound V | 0.01 |
| Monobasic sodium phosphate | 0.05 |
| Dibasic sodium phosphate (anhydrous) | 0.15 |
| Sodium chloride | 0.75 |
| Disodium EDTA (Edetate disodium) | 0.05 |
| CREMOPHOR ® EL | 0.1 |
| Benzalkonium chloride | 0.01 |
| HCl and/or NaOH | pH 7.3–7.4 |
| Purified water | q.s. to 100% |

EXAMPLE 7

| Ingredient | Amount (wt %) |
| --- | --- |
| Compound II | 0.1 |
| Phosphate Buffered Saline | 1.0 |
| Hydroxypropyl-$\beta$-cyclodextrin | 4.0 |
| Purified water | q.s. to 100% |

The invention has been described by reference to certain preferred embodiments; however, it should be understood that it may be embodied in other specific forms or variations thereof without departing from its spirit or essential characteristics. The embodiments described above are therefore considered to be illustrative in all respects and not restrictive, the scope of the invention being indicated by the appended claims rather than by the foregoing description.

What is claimed is:

1. A method of treating glaucoma or ocular hypertension in a patient, which comprises administering to the patient a pharmaceutically effective amount of a compound of formula I:

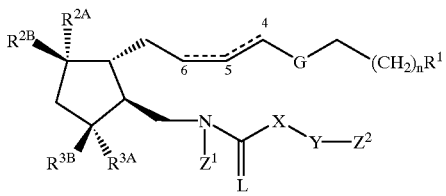

wherein:
$R^1$=$CO_2R$, $CONR^4R^5$, $CH_2OR^6$, or $CH_2NR^7R^8$; where:
R=H or cationic salt moiety, or $CO_2R$ forms a pharmaceutically acceptable ester moiety;
$R^4$, $R^5$=same or different=H or alkyl;
$R^6$=H, acyl, or alkyl;
$R^7$, $R^8$=same or different=H, acyl, or alkyl; with the proviso that if one of
$R^7$, $R^8$=acyl, then the other=H or alkyl;
n=0 or 2;
G=$CH_2$ or 0;
$R^{2A}$=H, OH, acyloxy, alkoxy;
$R^{2B}$=H, halogen, OH, acyloxy, alkoxy, with the provisos that if $R^{2B}$=halogen, then $R^{2A}$=H, and that $R^{2A}$ and $R^{2B}$ cannot both be from the group consisting of: OH, acyloxy, and alkoxy;
or, $R^{2A}R^{2B}$ taken together=O;
$R^{3A}$=H, OH, acyloxy, alkoxy;
$R^{3B}$=H, halogen, OH, acyloxy, alkoxy, with the provisos that if $R^{3B}$=halogen, then $R^{3A}$=H, and that $R^{3A}$ and $R^{3B}$ cannot both be from the group consisting of: OH, acyloxy, and alkoxy;
or, $R^{3A}R^{3B}$ together=O;
with the further provisos: that if one of $R^{2B}$, $R^{3B}$=halogen, then the other=H; that if one of $R^{2A}R^{2B}$ taken together or $R^{3A}R^{3B}$ taken together=O, then the other≠O; and that $R^{2A}$, $R^{2B}$, $R^{3A}$, $R^{3B}$ cannot all=H;
- - -=single or non-cumulated double bond, with the proviso that when G=O, a single bond exists between carbons 4 and 5;
$Z^1$=H or $CH_3$;
L=O or S;
X=O, S, NH, $CH_2$, or a direct bond;
Y=O, S, NH, $CH_2$, or a direct bond;
with the provisos that Y=$CH_2$ or a direct bond when X=O, S, or NH, and that X $CH_2$ or a direct bond when Y=O, S, or NH;
$Z^2$=$(CH_2)_qCH_3$, cycloalkyl, heteroaryl, or phenyl, the heteroaryl or phenyl being optionally substituted with alkyl, halo, trihalomethyl, alkoxy, acyl, acyloxy, amino, alkylamino, acylamino, or hydroxy;
q=0–5;
or, $Z^2$=$(CH_2)_pY^1$; where p=0–6; and

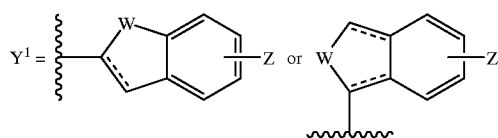

wherein:
W=$CH_2$, O, $S(O)_m$, $NR^9$, $CH_2CH_2$, CH═CH, $CH_2O$, $CH_2S(O)_m$, CH═N, or $CH_2NR^9$; where m=0–2, and $R^9$=H, alkyl, or acyl;

Z=H, alkyl, alkoxy, acyl, acyloxy, halo, trihalomethyl, amino, alkylamino, acylamino, or hydroxy; and
- - -=single or double bond.

2. The method of claim 1, wherein the compound is administered topically.

3. The method of claim 2, wherein the compound is administered as a solution, suspension, or emulsion in an ophthalmically acceptable vehicle.

4. The method of claim 2, wherein the concentration of the compound is between about 0.00003 to about 0.5 weight percent.

5. The method of claim 4, wherein the concentration of the compound is between about 0.0005 to about 0.03 weight percent.

6. The method of claim 5, wherein the concentration of the compound is between about 0.001 to about 0.01 weight percent.

7. The method of claim 1, wherein for the compound of formula I:

$R^1$=$CO_2R$, where R=H or $CO_2R$ forms an ophthalmically acceptable ester moiety;

n=0;

G=$CH_2$ or O, with the proviso that G=$CH_2$ when $R^{2A}$=OH;

- - -=a single or non-cumulated double bond, with the provisos that a double bond between carbons 4 and 5 may not be of the trans configuration and that a single bond exists between carbons 4 and 5 when G=O;

$R^{2A}$=OH, and $R^{2B}$=H; or $R^{2A}$=H, and $R^{2B}$=Cl;

$R^{3A}$=OH, and $R^{3B}$=H;

$Z^1$=H;

L=O;

X=$CH_2$ or a direct bond;

Y=$CH_2$, O, or a direct bond; and $Z^2$=phenyl optionally substituted with halo or trihalomethyl;

or $Z^2$=cyclohexyl;

or $Z^2$=$Y^1$, where

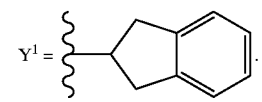

8. The method of claim 7, wherein the compound is:

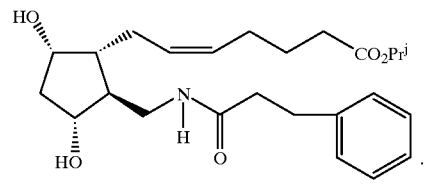

9. The method of claim 7, wherein the compound is:

[Chemical structure]

10. The method of claim 7, wherein the compound is:

[Chemical structure]

11. The method of claim 7, wherein the compound is:

[Chemical structure]

12. A compound of formula I:

[Chemical structure I]

wherein:
$R^1$=$CO_2R$, $CONR^4R^5$, $CH_2OR^6$, or $CH_2NR^7R^8$; where:
R=H or cationic salt moiety, or $CO_2R$ forms a pharmaceutically acceptable ester moiety;
$R^4$, $R^5$=same or different=H or alkyl;
$R^6$=H, acyl, or alkyl;
$R^7$, $R^8$=same or different=H, acyl, or alkyl; with the proviso that if one of
$R^7$, $R^8$=acyl, then the other=H or alkyl;
n=0 or 2;
G=$CH_2$ or O;
$R^{2A}$=H, OH, acyloxy, alkoxy;
$R^{2B}$=H, halogen, OH, acyloxy, alkoxy, with the provisos that if $R^{2B}$=halogen, then $R^{2A}$=H, and that $R^{2A}$ and $R^{2B}$ cannot both be from the group consisting of: OH, acyloxy, and alkoxy;
or, $R^{2A}R^{2B}$ taken together=O;
$R^{3A}$=H, OH, acyloxy, alkoxy;
$R^{3B}$=H, halogen, OH, acyloxy, alkoxy, with the provisos that if $R^{3B}$=halogen, then $R^{3A}$=H, and that $R^{3A}$ and $R^{3B}$ cannot both be from the group consisting of: OH, acyloxy, and alkoxy;
or, $R^{3A}R^{3B}$ together=O;
with the further provisos: that if one of $R^{2B}$, $R^{3B}$=halogen, then the other=H; that if one of $R^{2A}R^{2B}$ taken together or $R^{3A}R^{3B}$ taken together=O, then the other≠O; and that $R^{2A}$, $R^{2B}$, $R^{3A}$, $R^{3B}$ cannot all=H;

- - -=single or non-cumulated double bond, with the proviso that when G=O, a single bond exists between carbons 4 and 5;

$Z^1$=H or $CH_3$;
L=O or S;
X=O, S, NH, $CH_2$, or a direct bond;
Y=O, S, NH, $CH_2$, or a direct bond;
with the provisos that Y=$CH_2$ or a direct bond when X=O, S, or NH, and that X $CH_2$ or a direct bond when Y=O, S, or NH;
$Z^2$=$(CH_2)_qCH_3$, cycloalkyl, heteroaryl, or phenyl, the heteroaryl or phenyl being optionally substituted with alkyl, halo, trihalomethyl, alkoxy, acyl, acyloxy, amino, alkylamino, acylamino, or hydroxy;
q=0–5;
or, $Z^2$=$(CH_2)_pY^1$; where p=0–6; and

[Chemical structure showing $Y^1$ definitions]

wherein:

W=$CH_2$, O, $S(O)_m$, $NR^9$, $CH_2CH_2$, CH=CH, $CH_2O$, $CH_2S(O)_m$, CH=N, or $CH_2NR^9$; where m=0–2, and $R^9$=H, alkyl, or acyl;

Z=H, alkyl, alkoxy, acyl, acyloxy, halo, trihalomethyl, amino, alkylamino, acylamino, or hydroxy; and

- - -=single or double bond.

13. The compound of claim 12, wherein:

$R^1$=$CO_2R$, where R=H or $CO_2R$ forms an ophthalmically acceptable ester moiety;

n=0;

G=$CH_2$ or O, with the proviso that G=$CH_2$ when $R^{2A}$=OH;

- - -=a single or non-cumulated double bond, with the provisos that a double bond between carbons 4 and 5 may not be of the trans configuration and that a single bond exists between carbons 4 and 5 when G=O;

$R^{2A}$=OH, and $R^{2B}$=H; or $R^{2A}$=H, and $R^{2B}$=Cl;

$R^{3A}$=OH, and $R^{3B}$=H;

$Z^1$=H;

L=O;

X=CH$_2$ or a direct bond;

Y=CH$_2$, O, or a direct bond; and

Z$^2$=phenyl optionally substituted with halo or trihalomethyl;

or Z$^2$=cyclohexyl;

or Z$^2$=Y$^1$, where

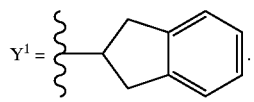

14. The compound of claim 13, having the formula:

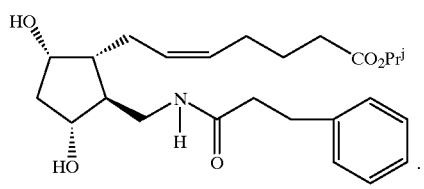

15. The compound of claim 13, having the formula:

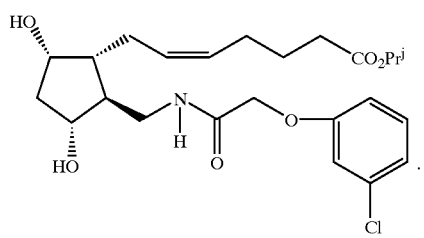

16. The compound of claim 13, having the formula:

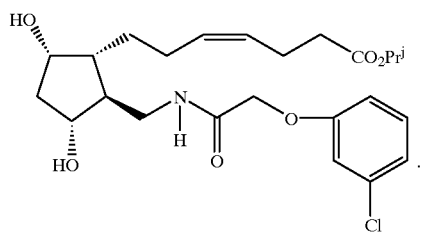

17. The compound of claim 13, having the formula:

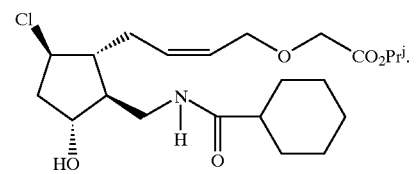

18. An ophthalmic composition for the treatment of glaucoma and ocular hypertension, comprising a compound of formula I:

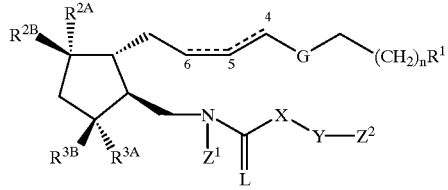

wherein:

R$^1$=CO$_2$R, CONR$^4$R$^5$, CH$_2$OR$^6$, or CH$_2$NR$^7$R$^8$; where:
R=H or cationic salt moiety, or CO$_2$R forms a pharmaceutically acceptable ester moiety;
R$^4$, R$^5$=same or different=H or alkyl;
R$^6$=H, acyl, or alkyl;
R$^7$, R$^8$=same or different=H, acyl, or alkyl; with the proviso that if one of
R$^7$, R$^8$=acyl, then the other=H or alkyl;

n=0 or 2;

G=CH$_2$ or O;

R$^{2A}$=H, OH, acyloxy, alkoxy;

R$^{2B}$=H, halogen, OH, acyloxy, alkoxy, with the provisos that if R$^{2B}$=halogen, then R$^{2A}$=H, and that R$^{2A}$ and R$^{2B}$ cannot both be from the group consisting of: OH, acyloxy, and alkoxy;

or, R$^{2A}$R$^{2B}$ taken together=O;

R$^{3A}$=H, OH, acyloxy, alkoxy;

R$^{3B}$=H, halogen, OH, acyloxy, alkoxy, with the provisos that if R$^{3B}$=halogen, then R$^{3A}$=H, and that R$^{3A}$ and R$^{3B}$ cannot both be from the group consisting of: OH, acyloxy, and alkoxy;

or, R$^{3A}$R$^{3B}$ taken together=O;

with the further provisos: that if one of R$^{2B}$, R$^{3B}$=halogen, then the other=H; that if one of R$^{2A}$R$^{2B}$ taken together or R$^{3A}$R$^{3B}$ taken together=O, then the other≠O; and that R$^{2A}$, R$^{2B}$, R$^{3A}$, R$^{3B}$ cannot all=H;

- - - =single or non-cumulated double bond, with the proviso that when G=O, a single bond exists between carbons 4 and 5;

Z$^1$=H or CH$_3$;

L=O or S;

X=O, S, NH, CH$_2$, or a direct bond;

Y=O, S, NH, CH$_2$, or a direct bond;

with the provisos that Y=CH$_2$ or a direct bond when X=O, S, or NH, and that X CH$_2$ or a direct bond when Y=O, S, or NH;

Z$^2$=(CH$_2$)$_q$CH$_3$, cycloalkyl, heteroaryl, or phenyl, the heteroaryl or phenyl being optionally substituted with alkyl, halo, trihalomethyl, alkoxy, acyl, acyloxy, amino, alkylamino, acylamino, or hydroxy;

q=0–5;

or, Z$^2$=(CH$_2$)$_p$Y$^1$; where p=0–6; and

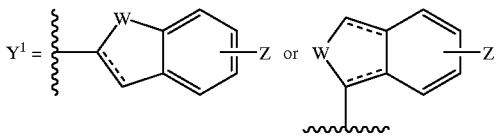

wherein:

W=CH$_2$, O, S(O)$_m$, NR$^9$, CH$_2$CH$_2$, CH=CH, CH$_2$O, CH$_2$S(O)$_m$, CH=N, or CH$_2$NR$^9$; where m=0–2, and R$^9$=H, alkyl, or acyl;

Z=H, alkyl, alkoxy, acyl, acyloxy, halo, trihalomethyl, amino, alkylamino, acylamino, or hydroxy; and ----=single or double bond.

19. The composition of claim 18, wherein for the compound of formula I:

R$^1$=CO$_2$R, where R=H or CO$_2$R forms an ophthalmically acceptable ester moiety;

n=0;

G=CH$_2$ or O, with the proviso that G=CH$_2$ when R$^{2A}$=OH;

----=a single or non-cumulated double bond, with the provisos that a double bond between carbons 4 and 5 may not be of the trans configuration and that a single bond exists between carbons 4 and 5 when G=O;

R$^{2A}$=OH, and R$^{2B}$=H; or R$^{2A}$=H, and R$^{2B}$=Cl;

R$^{3A}$=OH, and R$^{3B}$=H;

Z$^1$=H;

L=O;

X=CH$_2$ or a direct bond;

Y=CH$_2$, O, or a direct bond; and

Z$^2$=phenyl optionally substituted with halo or trihalomethyl;

or Z$^2$=cyclohexyl;

or Z$^2$=Y$^1$, where

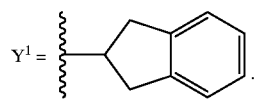

20. The composition of claim 19, wherein the compound has the following formula:

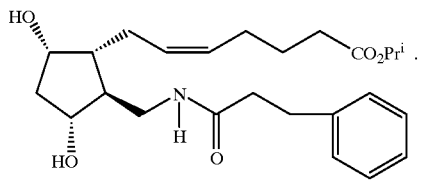

21. The composition of claim 19, wherein the compound has the following formula:

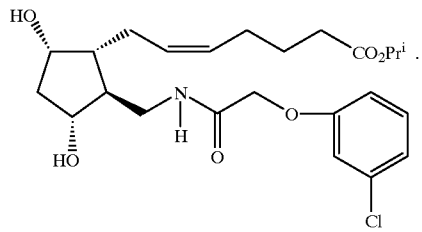

22. The composition of claim 19, wherein the compound has the following formula:

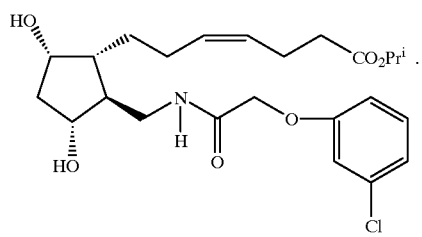

23. The composition of claim 19, wherein the compound has the following formula:

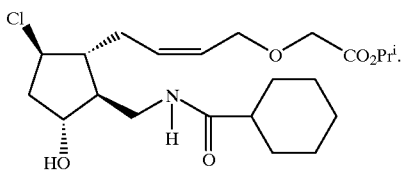

\* \* \* \* \*